US008235890B2

(12) United States Patent
Wendlandt et al.

(10) Patent No.: US 8,235,890 B2
(45) Date of Patent: *Aug. 7, 2012

(54) ENDOSCOPIC VISION SYSTEM

(75) Inventors: Jeffrey M. Wendlandt, Newton, MA (US); Mark L. Adams, Sloughton, MA (US)

(73) Assignee: Boston Scientific Scimed, Inc., Natick, MA (US)

( * ) Notice: Subject to any disclaimer, the term of this patent is extended or adjusted under 35 U.S.C. 154(b) by 267 days.

This patent is subject to a terminal disclaimer.

(21) Appl. No.: 12/461,515

(22) Filed: Aug. 13, 2009

(65) Prior Publication Data
US 2010/0041947 A1    Feb. 18, 2010

Related U.S. Application Data

(63) Continuation of application No. 11/302,215, filed on Dec. 14, 2005, now Pat. No. 7,591,785, which is a continuation of application No. 10/722,141, filed on Nov. 26, 2003, now Pat. No. 7,004,900, which is a continuation of application No. 09/768,337, filed on Jan. 25, 2001, now Pat. No. 6,736,773.

(51) Int. Cl.
*A61B 1/06* (2006.01)
*A61B 1/04* (2006.01)

(52) U.S. Cl. .................... 600/173; 600/109

(58) Field of Classification Search ........... 600/103, 600/109, 113, 129, 166, 173–175
See application file for complete search history.

(56) References Cited

U.S. PATENT DOCUMENTS

| 3,871,365 | A | 3/1975 | Chikama |
| 4,976,524 | A | 12/1990 | Chiba |
| 5,215,077 | A | 6/1993 | Oku |
| 5,373,840 | A | 12/1994 | Knighton |
| 5,381,784 | A * | 1/1995 | Adair .................. 600/166 |
| 5,448,990 | A | 9/1995 | De Faria-Correa |
| 5,533,496 | A | 7/1996 | De Faria-Correa et al. |
| 5,582,576 | A | 12/1996 | Hori et al. |
| 5,762,603 | A | 6/1998 | Thompson |
| 6,184,923 | B1 | 2/2001 | Miyazaki |
| 6,736,773 | B2 | 5/2004 | Wendlandt et al. |
| 7,004,900 | B2 | 2/2006 | Wendlandt et al. |
| 2002/0099276 | A1 | 7/2002 | Wendlandt et al. |
| 2004/0254423 | A1 | 12/2004 | Wendlandt et al. |
| 2006/0106286 | A1 | 5/2006 | Wendlandt et al. |

FOREIGN PATENT DOCUMENTS
DE    29716512 U1    10/1997
* cited by examiner

*Primary Examiner* — Philip R Smith
(74) *Attorney, Agent, or Firm* — Finnegan, Henderson, Farabow, Garrett & Dunner, LLP

(57) ABSTRACT

The present invention relates to an endoscopic visioning system and related method for both forward and backward viewing of a body lumen. According to an embodiment, the system includes an endoscope, a vision head including a light source and a vision chip on both a proximal and a distal side of the vision head, and an extension arm for moving the vision head away from and back toward the endoscope. Alternatively, the light source and vision chip may be contained in a distal end of the endoscope. In such an alternative embodiment, the vision head is a parabolic mirror mounted on the extension arm for reflecting images, for example, from behind the distal end of the endoscope to the vision chip in the distal end of the endoscope to permit, for example, a retrograde view of the surgical site entrance.

14 Claims, 5 Drawing Sheets

ENDOSCOPIC VISION SYSTEM

This is a continuation of application Ser. No. 11/302,215, filed Dec. 14, 2005 now U.S. Pat. No. 7,591,785, which is a continuation of application Ser. No. 10/722,141, filed Nov. 26, 2003, now U.S. Pat. No. 7,004,900, issued Feb. 28, 2006, which is a continuation of application Ser. No. 09/768,337, filed Jan. 25, 2001, now U.S. Pat. No. 6,736,773, issued May 18, 2004, all of which are incorporated herein by reference.

BACKGROUND OF THE INVENTION

1. Field of the Invention

The present invention relates to an endoscopic vision system and a related method of viewing a body lumen.

2. Background of the Related Art

Millions of endoluminal procedures are performed each year. An endoluminal procedure takes place within a tube, or lumen, of the human body, such as a vascular, gastrointestinal, or air exchange lumen, and generally involves the diagnosis and/or treatment of diseases. Endoluminal procedures generally involve use of an endoscope, a rigid or flexible tube which can be introduced into the human body through the entrance to a lumen of the body, such as the mouth or rectum. Alternatively, an endoscope may be inserted into the human body through an incision made by a surgeon. The endoscope allows the surgeon to view the patient and an intended surgical site internally without the surgeon being in a direct line of sight with the object or area being viewed. The endoscope provides one or more open, working channels, or pathways, between a desired surgical site and the surgeon. An endoscope may carry, for example, one or more lights, visioning systems, and other tools, such as diagnostic and treatment devices that extend from a proximal end near by the surgeon, through the working channel, and to the distal end at a surgical site. The size of the endoscope used may vary, depending on the particular lumen of the patent and the size and number of instruments which need to be introduced to the surgical site.

Endoscopes typically are manually inserted into the patient by the surgeon and manually steered or positioned by the surgeon or nurse by pushing the endoscope through the body until the endoscope is properly positioned. Dependent upon the size and flexibility of the endoscope used, forcing the endoscope into a lumen of the patient may traumatize the surrounding tissues. Thus, the ability to visualize the area into which the endoscope is being inserted is important. To view the area, an endoscope may communicate with a monitor to display the field of view. However, lack of an to adequate field of vision, poor resolution, and poor illumination are problems in existing endoscopic visioning systems which make it difficult for a surgeon to view the surgical area and accurately position an endoscope.

FIGS. 1 and 2 illustrate an embodiment of a conventional endoscope. It includes an insertion tube, a lumen or working channel within the insertion tube, a light source and a vision chip. Such an endoscope has several limitations. For example, the opening to the working channel, the light source, and the vision chip are each restricted to, for example, a couple of millimeters in diameter. This compromises performance of the visioning system and increases costs for components of the system due to the need to miniaturize the components. The limited space available on a working end of a conventional endoscope restricts the size of the visioning system. Such visioning elements also take away needed space for the working channel(s) of the endoscope—limiting the size and number of the tools which can pass through the working channel.

Larger, more rigid endoscopes can support larger, more powerful light sources for better illumination and larger vision chips for better resolution. Such endoscopes, however, lack flexibility, making it more difficult to maneuver the endoscope within the body. Smaller, articulating endoscopes are much more flexible but are relatively small in diameter, and thus lack the size necessary to support larger illumination and resolution elements.

In addition, such a system is only forward-looking, and has a relatively narrow field of vision, with a viewing angle of, for example, about 120 degrees, as shown in FIG. 2. This makes it extremely difficult for a surgeon to view the region where the endoscope enters the body lumen. Very flexible endoscopes may perform what is known as a "scope-retrograde" maneuver, in which the endoscope bends back upon itself to allow the user to visualize the endoscope's point of entry. Such endoscopes are expensive, require expertise on the part of the operator, and require space within the body lumen to perform such a maneuver.

In light of the difficulty in positioning devices introduced into the human body through endoscopes, the difficulty in maximizing working channel space, and the difficulty of providing adequate illumination, resolution, and field of vision in existing visioning systems for endoscopes, there is a need for a method and device which solve these problems.

SUMMARY OF THE INVENTION

In light of the drawbacks of the visioning systems described, there is a need for an endoscopic visioning system capable of providing an adequate field of vision, improved illumination and resolution, and increased working channel space. Accordingly, the present invention is directed to an improved device that obviates the limitations and disadvantages of conventional endoscopic visioning systems.

To achieve these and other advantages and in accordance with the present invention, as embodied and broadly described herein, an endoscopic device is provided. The endoscopic device includes an endoscope having proximal and distal ends, an extension arm passing through a channel in the endoscope to the distal end of the endoscope, and a head attached to a distal end of the extension arm wherein the head includes a vision member capable of receiving an image of a surgical site.

According to another aspect of the invention, the endoscopic device includes an endoscope having proximal and distal ends, an extension arm passing through a channel in the endoscope to the distal end of the endoscope, and a mirror attached to a distal end of the extension arm.

According to a further aspect of the invention, a method for viewing a surgical site in a body lumen is provided. The method includes placing a distal end of an endoscope into a body lumen, extending an extension arm to move a distal end of the extension arm away from a distal end of the endoscope, and viewing the surgical site with a vision member attached to the distal end of the extension arm, the surgical site being proximal to the vision member.

Additional features and advantages of the present invention will be set forth in the description which follows, and in part will be apparent from the description, or may be learned by practice of the invention. The objectives and advantages of the invention will be realized and attained by means of the elements and combinations particularly pointed out in the appended claims.

BRIEF DESCRIPTION OF THE DRAWINGS

The accompanying drawings, which are incorporated in and constitute a part of this specification, illustrate various embodiments of the invention and together with the description, serve to explain the principles of the invention. In the drawings.

DESCRIPTION OF THE PREFERRED EMBODIMENTS

Figure 1:
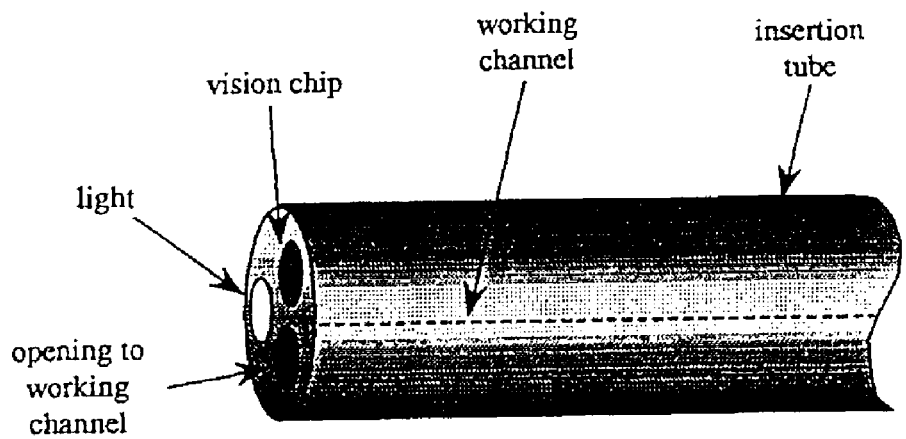
FIG. 1 is an isometric side view of an endoscope with a conventional visioning system.
Figure 2:
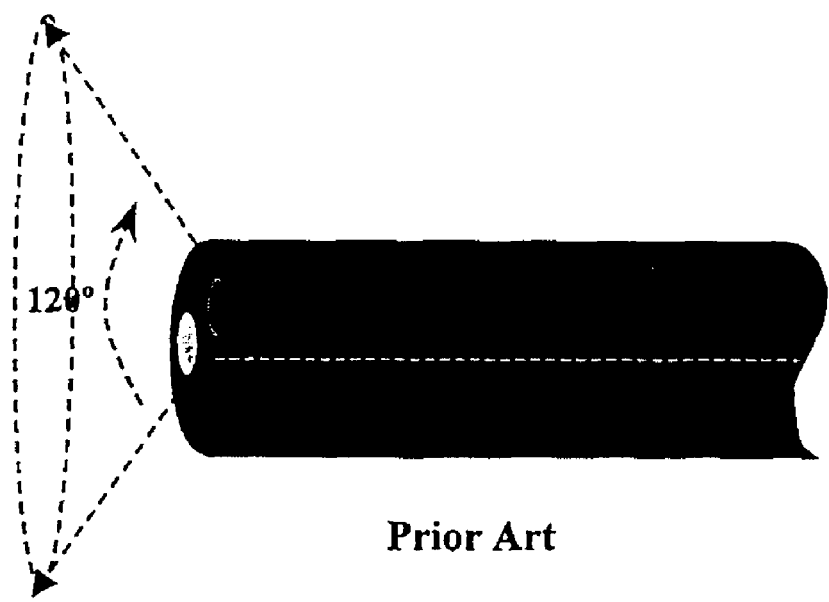
FIG. 2 is an isometric side view the endoscope of FIG. 1 displaying the field of vision for conventional endoscopic visioning systems.

Reference will now be made in detail to the present preferred embodiments of the invention, examples of which are illustrated in the accompanying drawings. Wherever possible, the same reference numbers will be used throughout the drawings to refer to the same or like parts.

According to the present invention, an endoscopic visioning system is provided. A first embodiment of the endoscopic visioning system includes an endoscope, an extension arm, and a vision head attached to the extension arm. The vision head is extensible within a body lumen away from and back toward the endoscope. The vision head is also rotatable and capable of being angled with respect to a longitudinal axis of the endoscope. The vision head preferably includes at least one vision chip and light source, and more preferably may include a vision chip and light source on both a proximal and a distal face of the vision head.

A second embodiment of the endoscopic visioning system includes an endoscope, an extension arm, and a mirror attached to the extension arm. The mirror is preferably a parabolic mirror. The mirror is extensible within a body lumen away from and back toward the endoscope. The mirror is also rotatable and capable of being angled with respect to a longitudinal axis of the endoscope. A distal end of the endoscope includes a vision chip and a light source. The reflective surface of the mirror faces the distal end of the endoscope such that an image of an area more toward the proximal end of the endoscope may reflect off of the mirror to the vision chip. The vision system preferably also includes distortion correction means for correcting distortion of the image due to the mirror. Preferably, the distortion correction means includes a digitizer in communication with appropriate computer software.

The use of an extensible vision head or mirror allows for better viewing as an endoscope enters the body and during further insertion of the endoscope into the body lumen. This allows for easier and more accurate positioning of the endoscope within the body. The improved accuracy reduces the amount of time needed for the surgery/treatment and reduces the risk of erroneously cutting/treating the wrong tissue. The ability to extend, rotate, and angle the vision head or mirror maximizes the field of vision of the user.

In addition, by separating the vision elements, such as the vision chip and light source, from the distal end of the endoscope, more space becomes available on the distal end and within the endoscope itself, i.e., there is no longer a need to provide space on the distal end of the endoscope for the vision chip and the light source. Thus, it is possible that the endoscope may have more than one lumen or a larger lumen (working channel) available to pass/contain tools for the surgery/treatment.

In addition, a mirror or a second set of vision elements on a proximal side of the vision head provides a surgeon with a view of the entry site of the endoscope within the body lumen or a view of other areas near the proximal end of the endoscope. There is no need for space within the body lumen to maneuver the endoscope back on itself to view the entry point, nor is there a need for an extremely flexible endoscope which cannot support the visioning system. In addition, this means that requirements for tools used within the endoscope will be less restrictive.

Figure 3:
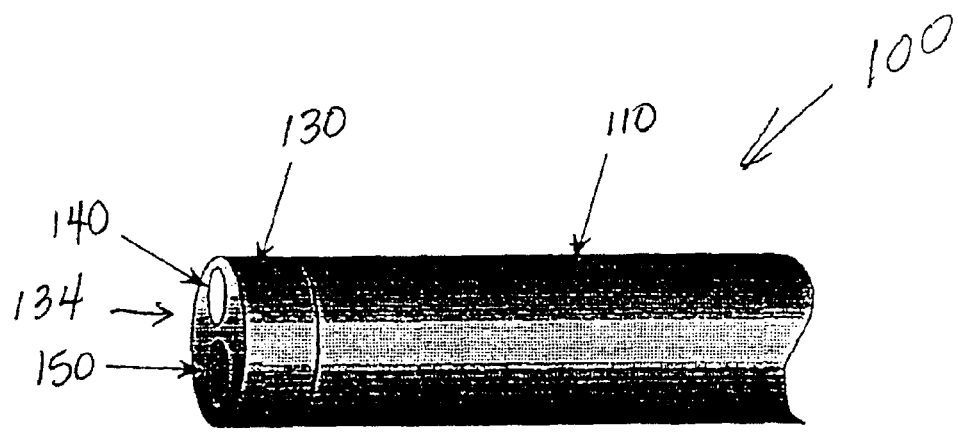
FIG. 3 is an isometric side view of an endoscope with a visioning system according to a first embodiment of the present invention.

According to a first preferred embodiment of the present invention and as shown in FIG. 3, an endoscopic visioning system 100 is provided. System 100 generally may include an endoscope, an extension arm, and a vision head. Each of these general portions of system 100 will be described in detail.

Figure 4:
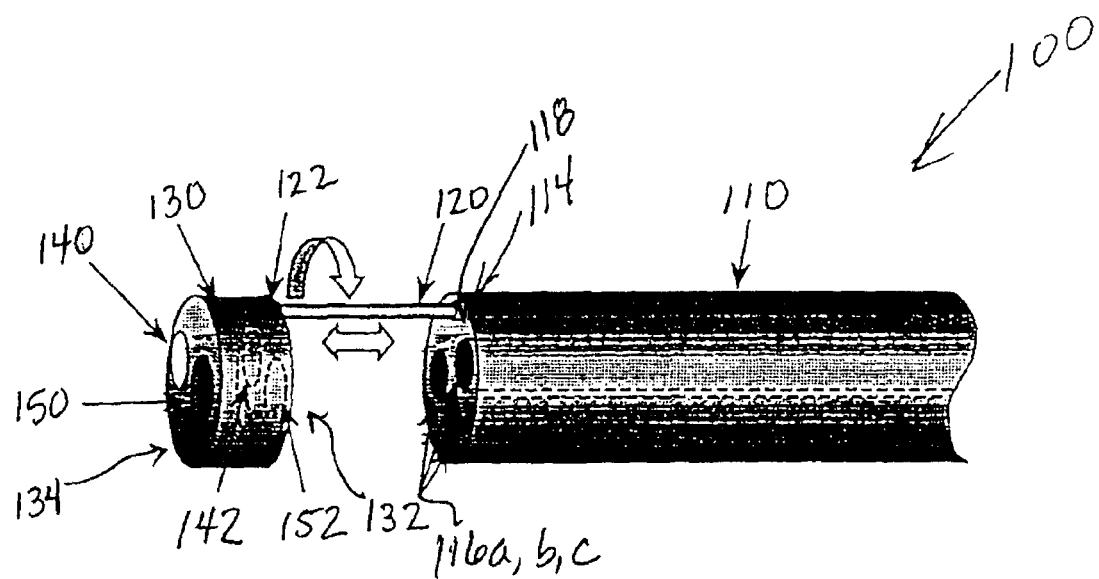
FIG. 4 is an isometric side view of the endoscope of FIG. 3 with a vision head in an extended position.
Figure 5:
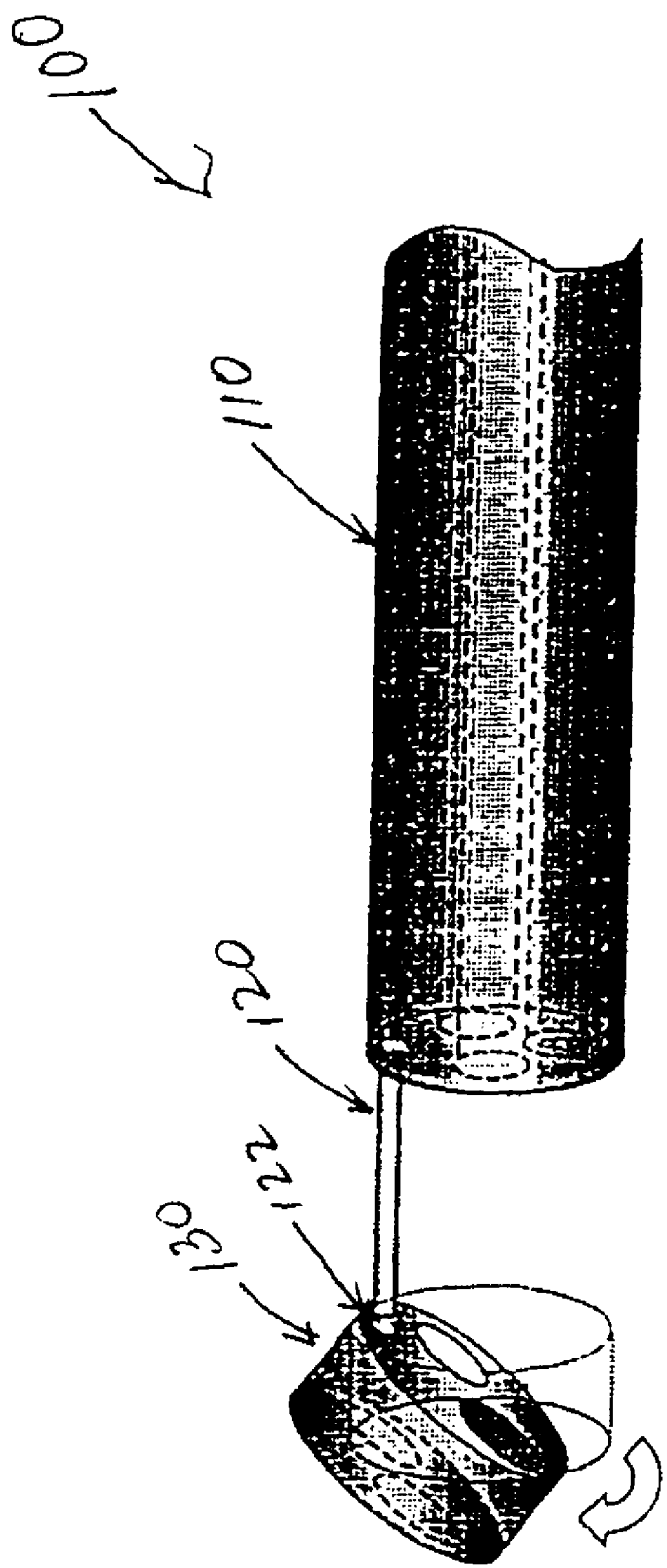
FIG. 5 is an isometric side view of the endoscope of FIG. 3 with a vision head in an angled position.

As embodied herein and shown in FIGS. 3-5, an endoscope 110 is provided. Endoscope 110 may be of any suitable diameter so as to be capable of insertion into a body lumen and to contain the necessary tools for a particular procedure to be performed in the body lumen. Endoscope 110 has a proximal end (not shown) and a distal end 114, wherein the distal end 114 is the end of endoscope 110 inserted into a body lumen. Endoscope 110 may be either a disposable endoscope or a reusable endoscope. If endoscope 110 is a reusable endoscope, it should be made from materials easily cleanable and sterilizable. If endoscope 110 is disposable, it may be made from any suitable biocompatible material, such as a plastic or other polymer. The exterior of endoscope 110 may have a hydrophilic coating to facilitate its passage through the body lumen. Endoscope 110 also includes at least one lumen or working channel 116a, 116b, 116c for receiving surgical instruments. Preferably endoscope 110 includes more than one lumen for receiving the surgical instruments. Endoscope 110 also includes a lumen 118 configured to receive an extension arm 120.

As embodied herein and shown in FIG. 3, endoscopic visioning system 100 also includes a vision head 130. Vision head 130 includes a proximal face 132 and a distal face 134. Vision head 130 is mounted on an extension arm 120 which passes through lumen 118 of endoscope 110. Vision head 130 is preferably mounted to extension arm 120 by a ball joint 122 but may be mounted by any other mechanical connection permitting articulating motion relative to extension arm 120. Ball joint 122 allows the vision head 130 to be angled with respect to a longitudinal axis of the endoscope 110. In addition, vision head 130 is rotatable about its longitudinal axis by rotation of the extension arm 120 within its lumen 118. Movement of the vision head 130 through extension arm 120 is preferably controlled from the proximal end of the endoscope 110 through any suitable actuator known in the art. Vision head 130 is moveable away from and back toward the distal end 114 of endoscope 110 on extension arm 120. When the vision head 130 is located next to the distal end 114 of endoscope 110, the proximal face 132 of vision head 130 is adjacent the distal end 114 of the endoscope 110. In a preferred embodiment, vision head 130 has a diameter approximately the same as a diameter of the endoscope 110. The vision head diameter, however, may be smaller or larger than that of the distal end of the endoscope should the need arise. Also in a preferred embodiment, the lumen for extension arm 120 is located towards the periphery of the distal end of the endoscope. The extension arm lumen, however, may be positioned at any other suitable location should it, for example, be desirable to locate all surgical instrument lumens along the periphery of the distal end of the endoscope. The extension arm 120 may be made of stainless steel, plastic, or other suitable materials, and the vision head 130 may be made of the same or similar materials as the endoscope. The extension arm 120 is preferably a rod or rigid tube, but may be in any other suitable form.

The distal face 134 of vision head 130 includes a distal light source 140 and a distal vision chip 150. Preferably, the proximal face 132 of vision head 130 also includes a proximal light source 142 and a proximal vision chip 152. The distal light source 140 and distal vision chip 150 allow for forward-looking vision within the body lumen. The proximal light source 142 and proximal vision chip 152 allow backward-looking (toward the entry site of the endoscope into the body lumen) vision or retrograde vision. Retrograde vision is only possible when the vision head 130 is extended away from the distal end 114 of the endoscope 110. Preferably, only one set of vision elements, forward-looking or backward-looking, is active at one time, which also may be controlled through appropriate structure at the proximal end of the endoscope.

Light sources 140, 142 are used to illuminate an area of which an image is to be taken. Vision chips 150, 152 obtain image information and pass video image data via electrical leads contained within the extension arm 120 to appropriate circuitry that will digitize the video data and communicate that data to a computer having suitable software to format the data and cause it to be displayed on a video display system located external to the endoscope. Extension arm 120 also contains electrical leads connected to an external power supply to supply power to the electronics contained in the vision head 130. Because all of the vision electronics are contained in the vision head 130, there is no need to have separate lumens leading to a light source and a vision chip. This results in additional space which can be used to pass surgical instruments to the surgical site.

In use, the distal face 134 of the vision head 130 is used to receive image information in front of (i.e., distal to) the endoscope 110. The distal face 134 may be extended (i.e., moved further away from the distal end 114 of the endoscope 110) in order to allow the user to get a closer view of an area of interest. Additionally, the distal face 134 may be extended, rotated, and angled by the user in a search for the optimal path for advancement of the entire endoscope further into the body cavity toward a desired surgical/treatment site, or to more closely view a surgical site, for example. Such manipulation of the vision head 130 maximizes the field of vision. The vision head 130 need not be extended, however, for the vision chip 150 to receive forward-looking image information.

To receive backward-looking or retrograde image data, the distal face 134 must be extended such that there is a space between the distal end 114 of the endoscope 110 and the proximal face 132 of the vision head 130. The further away the proximal face 132 of the vision head 130 is from the distal end 114 of the endoscope 110, the broader the view the proximal vision chip 152 will be able to image. In addition, the proximal face 132 may be extended, rotated, and angled, as controlled by a user from the proximal end of the endoscope 110, in order to obtain the clearest view of the point of entry of the endoscope into the body lumen. Such manipulation of the vision head 130 maximizes the field of vision.

In each case, forward-looking viewing or backward-looking viewing, the vision chip receives the image data. The vision chip passes image data, via leads in extension arm 120, to appropriate digitizing circuitry, appropriate computer software, and ultimately to a video display located external to the endoscope 110. The image is then viewed by the user on the display so that the user may further manipulate the endoscope and/or the endoscopic instruments therein for accurate positioning and treatment. Further manipulation of the position of the vision head will result in manipulation of the image viewed on the display.

Figure 6:
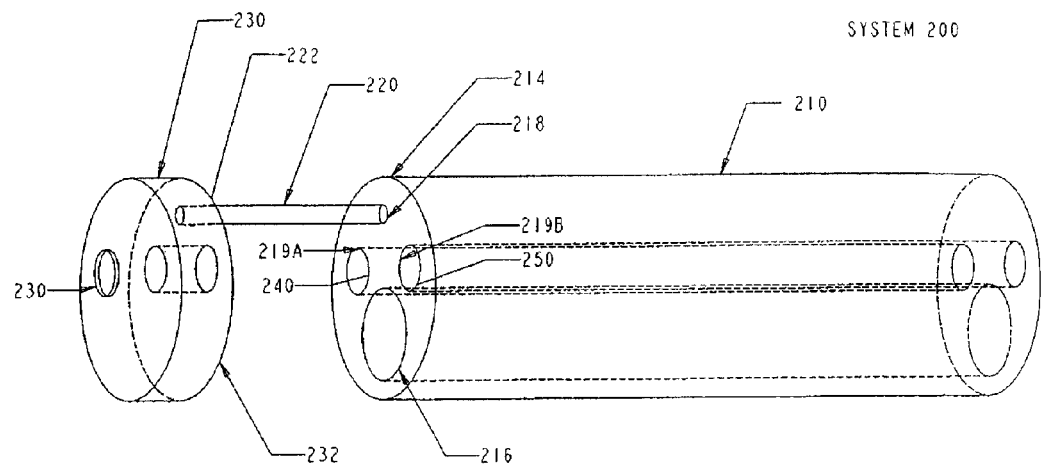
FIG. 6 is an isometric side view of an endoscope with a visioning system according to a second embodiment of the present invention.

According to a second preferred embodiment of the present invention and as shown in FIG. 6, an endoscopic visioning system 200 is provided. System 200 generally may include an endoscope, an extension arm, and a mirror. Each of these general portions of system 200 will be described in detail.

Figure 7:
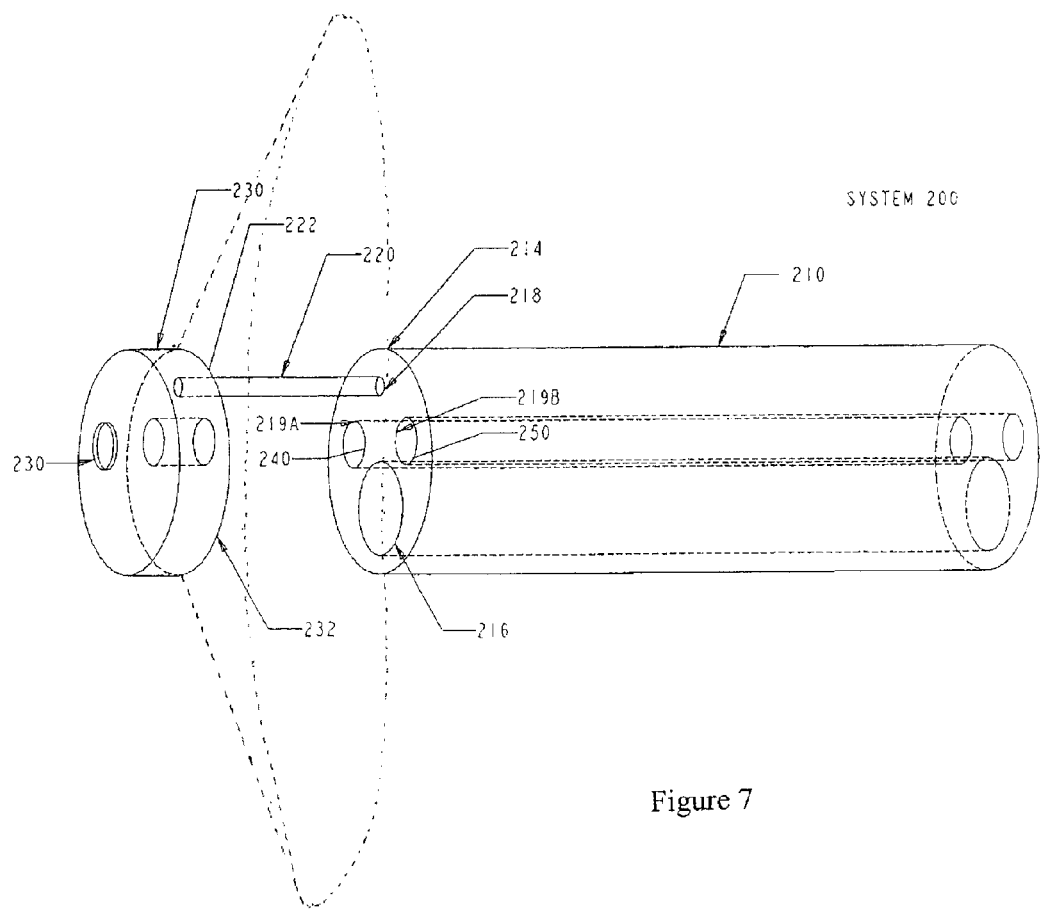
FIG. 7 is an isometric side view of the endoscope of FIG. 6 showing the field of vision for the visioning system of the endoscope of FIG. 6.

As embodied herein and shown in FIGS. 6 and 7, an endoscope 210 is provided. Endoscope 210 may be of any suitable diameter so as to be capable of insertion into a body lumen and to contain the necessary tools for a particular procedure to be performed in the body lumen. Endoscope 210 has a proximal end (not shown) and a distal end 214, wherein distal end 214 is the end of endoscope 210 inserted into a body lumen. Endoscope 210 may be either a disposable endoscope or a reusable endoscope. The exterior of endoscope 210 may have a hydrophilic coating to facilitate its passage through the body lumen. Endoscope 210 also includes at least one lumen or working channel 216 for receiving for receiving surgical instruments. Endoscope 210 also includes a lumen 218 configured to receive an extension arm 220, lumen 219a configured to receive appropriate elements for connection to a light source 240, and lumen 219b configured to receive appropriate elements for connection to a vision chip 250 at the distal end 214.

As embodied herein and shown in FIGS. 6 and 7, endoscopic visioning system 200 also includes a mirror 230. Mirror 230 is preferably a parabolic mirror. Mirror 230 includes a proximal parabolic reflective face 232. Mirror 230 is mounted on an extension arm 220 which passes through lumen 218 of endoscope 210. Mirror 230 is preferably mounted to extension arm 220 by a ball joint 222 but may be mounted by any other suitable mechanical connection to extension arm 220. If a flat mirror is used instead of a parabolic mirror, ball joint 222 may allow the mirror to be angled with respect to a longitudinal axis of the endoscope 210. Preferably, parabolic mirror 230 is not rotatable about its longitudinal axis by rotation of the extension arm 220. Alternatively, if a flat mirror is used instead of a parabolic mirror, it may be desirable to provide rotation of the mirror about its longitudinal axis. In addition, rotation of the mirror may allow movement of the mirror out of the line of sight of a vision chip 250 which is carried in the distal end 214 of the endoscope 210. Movement of either a parabolic mirror or a flat mirror out of the line of sight of the vision chip 250 will permit gathering of forward-looking image data.

Movement of the mirror 230 through extension arm 220 is preferably controlled from the proximal end of the endoscope 210 through any suitable actuator known in the art. Mirror 230 is moveable away from and back toward the distal end 214 of endoscope 210 on extension arm 220. When the mirror 230 is located next to the distal end 214 of endoscope 210, the parabolic reflective face 232 of mirror 230 is adjacent the distal end 214 of the endoscope 210. In a preferred embodiment, parabolic mirror 230 has a diameter approximately the same as a diameter of the endoscope 210. The mirror diameter, however, may be smaller or larger than that of the distal end of the endoscope should the need arise. Also in a preferred embodiment, the lumen for extension arm 220 is located towards the periphery of the distal end of the endoscope. The extension arm lumen, however, may be positioned at any other suitable location should it, for example, be desirable to locate all surgical instrument lumens along the periphery of the distal end of the endoscope. The extension arm 220 may be made of stainless steel, plastic, or other suitable materials, and the mirror 230 may be made of any suitable reflective materials. The extension arm 220 is preferably a rod or rigid tube, but may be in any other suitable form.

The distal face 214 of endoscope 210 includes the light source 240 and the vision chip 250. The light source 240 and vision chip 250, when used without mirror 230, allow for forward-looking vision within the body lumen. The light source 240 and vision chip 250, when used in conjunction with mirror 230, allow backward-looking (toward the entry site of the endoscope) vision or retrograde vision as shown in FIG. 7. Retrograde vision is possible when the mirror 230 is extended away from the distal end 214 of the endoscope 210 and is substantially aligned (i.e., is concentric with endoscope 210) to reflect an image back to vision chip 250. If mirror 230 is rotated to become unaligned with the distal end 214 of endoscope 210, it is possible for vision chip 250 to receive forward-looking image data and pass such data to appropriate electronic circuitry and software and preferably to a video display located external to the endoscope 210 through appropriate interfaces. When mirror 230 is aligned with vision chip 250, a retrograde or backward-looking image is reflected off of the reflective surface 232 of mirror 230 to vision chip 250. The received image data is then sent from vision chip 250 to be displayed.

Figure 8:
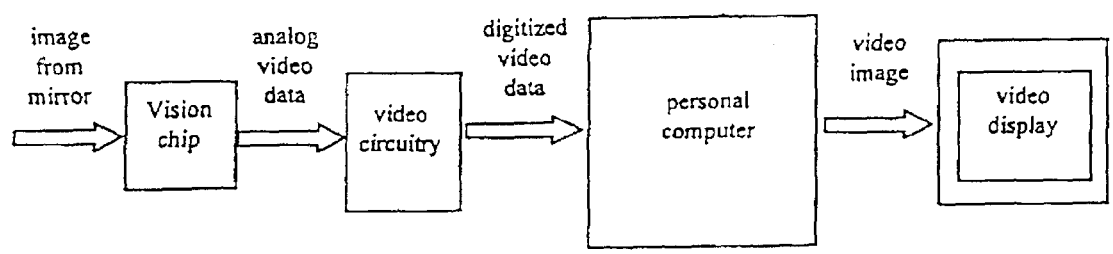
FIG. 8 is a flow chart showing the process used to correct distortion in the visioning system of the endoscope of FIG. 6.

The parabolic mirror, in use, provides a viewing angle of nearly 180 degrees facing the entry point (i.e., towards the proximal end) of the endoscope 210 within the body lumen (see FIG. 7). Use of the parabolic mirror, while providing a very wide viewing angle, also introduces a large amount of spherical distortion of the video image. The current invention corrects for this distortion by digitizing the image data and using appropriate computer software to correct the image to an orthographic format. The process for correcting for the distortion is shown in the flowchart of FIG. 8. The vision chip 250 collects video images reflected from the reflective surface 232 of mirror 230 and relays the analog video data to a video circuit board, preferably within a computer. The analog data is then converted to digital data. Next, the digitized data is operated on by a computer program run on the computer to remove the spherical distortion. An example of a program which can perform this function is OMNIVIDEO, written by researchers at Columbia University, and available at the website www.cs.columbia.edu/CAVE/omnicam/. This software is exemplary only, and other suitable software may be developed for use with this invention.

Once the image has been made distortion free, it is displayed on the video display connected to the computer. The software provides the user with a distortion free image within the overall field of view from the mirror. That view can be changed in magnification and direction in real-time, without changing the position of the endoscope 210, via commands issued to the system through a suitable program user interface known to persons skilled in the art. In addition, the breadth of the view can be increased or decreased by extending or retracting, respectively, the mirror 230 with respect to the distal end 214 of the endoscope 210.

Alternatively, as discussed above, if a flat mirror is used instead of a parabolic mirror, the mirror may be angled with respect to the extension arm 220 to obtain a different view. Further, rotation of a flat mirror about its longitudinal axis may also provide a different view. As with the parabolic mirror, the breadth and detail of the view can be increased or decreased by extending or retracting, respectively, the mirror 230 with respect to the distal end 214 of the endoscope 210.

It will be apparent to those skilled in the art that various modifications and variations can be made in the system of the present invention and in construction of the system without departing from the scope or spirit of the invention. Other embodiments of the invention will be apparent to those skilled in the art from consideration of the specification and practice of the invention disclosed herein. It is intended that the specification and examples be considered as exemplary only.

What is claimed is:

1. An endoscopic device, comprising:
   an endoscope including a lumen;
   an elongate member extending through the lumen in the endoscope;
   a first vision chip connected to a distal end of the elongate member configured to extend away from a distal end of the endoscope and obtain a backward-looking image; and a second vision chip configured to obtain a forward-looking image;
   wherein movement of the elongate member in a distal direction is configured to cause the first vision chip to extend away from the distal end of the endoscope.

2. The endoscopic device of claim 1, wherein the first vision chip is configured to articulate with respect to a longitudinal axis of the endoscope.

3. The endoscopic device of claim 1, wherein the first vision chip is configured to rotate about a longitudinal axis of the elongate member.

4. The endoscopic device of claim 1, wherein the first vision chip is configured to send the backward-looking image to a video display system, and the second vision chip is configured to send the forward-looking image to the video display system.

5. The endoscopic device of claim 1, wherein the elongate member contains electrical leads configured to power the first vision chip.

6. An endoscopic device, comprising:
   an endoscope including a lumen;
   an elongate member extending through the lumen in the endoscope;
   a first vision chip connected to a distal end of the elongate member configured to extend away from a distal end of the endoscope and obtain a backward-looking image;
   a second vision chip configured to obtain a forward-looking image; and
   a first light source connected to the distal end of the elongate member.

7. The endoscopic device of claim 6, further comprising a second light source.

8. An endoscopic device, comprising:
   an elongate member configured to extend through a lumen in an endoscope; and
   a first vision chip connected to a distal end of the elongate member and configured to extend away from a distal end of the endoscope, obtain a backward-looking image, and articulate with respect to a longitudinal axis of the endoscope;
   wherein the first vision chip is configured to rotate about the longitudinal axis of the endoscope.

9. An endoscopic device, comprising:
an elongate member configured to extend through a lumen in an endoscope;
a first vision chip connected to a distal end of the elongate member and configured to extend away from a distal end of the endoscope, obtain a backward-looking image, and articulate with respect to a longitudinal axis of the endoscope; and
a first light source connected to the distal end of the elongate member.

10. An endoscopic apparatus, comprising:
an endoscope including a lumen;
an elongate member extending through the lumen;
a vision head connected to a distal end of the elongate member and configured to articulate with respect to a longitudinal axis of the endoscope, the vision head having a first vision chip configured to obtain a backward-looking image; and
a second vision chip configured to obtain a forward-looking image
wherein the vision head is configured to stop in the absence of an external force in at least two different positions in which the vision head is extended away from a distal end of the endoscope.

11. The endoscopic device of claim 10, wherein the vision head is configured to rotate axis of the endoscope.

12. The endoscopic device of claim 10, wherein the vision head is configured to move away from and toward the distal end of the endoscope.

13. An endoscopic apparatus, comprising:
an endoscope including a lumen;
an elongate member extending through the lumen;
a vision head connected to a distal end of the elongate member and configured to articulate with respect to a longitudinal axis of the endoscope, the vision head having a first vision chip configured to obtain a backward-looking image;
a second vision chip configured to obtain a forward-looking image; and
a first light source connected to the distal end of the elongate member.

14. The endoscopic apparatus of claim 13, further comprising a second light source.

* * * * *

UNITED STATES PATENT AND TRADEMARK OFFICE
CERTIFICATE OF CORRECTION

| | | |
|---|---|---|
| PATENT NO. | : 8,235,890 B2 | Page 1 of 1 |
| APPLICATION NO. | : 12/461515 | |
| DATED | : August 7, 2012 | |
| INVENTOR(S) | : Jeffrey M. Wendlandt et al. | |

It is certified that error appears in the above-identified patent and that said Letters Patent is hereby corrected as shown below:

Claim 11, col. 10, lines 1-2, "vision head is configured to rotate axis of the endoscope" should read --vision head is configured to rotate about a longitudinal axis of the endoscope--.

Signed and Sealed this
Second Day of October, 2012

David J. Kappos
*Director of the United States Patent and Trademark Office*